United States Patent [19]

Nössner et al.

[11] Patent Number: 5,637,577

[45] Date of Patent: Jun. 10, 1997

[54] PHOSPHOLIPID DERIVATIVES CONTAINING HIGHER ELEMENTS OF THE FIFTH GROUP

[75] Inventors: Gerhard Nössner; Jurij Stekar, both of Offenbach; Peter Hilgard, Frankfurt; Bernhard Kutscher, Maintal; Jurgen Engel, Alzenau, all of Germany

[73] Assignee: Asta Medica Aktiengesellschaft, Dresden, Germany

[21] Appl. No.: 421,920

[22] Filed: Apr. 14, 1995

Related U.S. Application Data

[62] Division of Ser. No. 124,492, Sep. 22, 1993, Pat. No. 5,449,798.

[30] Foreign Application Priority Data

Oct. 1, 1992 [DE] Germany ............................ 42 33 044.0

[51] Int. Cl.$^6$ .................. A61K 31/66; A61K 31/555; A61K 31/34
[52] U.S. Cl. .................. 514/105; 514/184; 514/461; 514/473; 549/472; 556/18; 556/30; 556/70; 556/76; 558/81; 558/82; 558/155; 558/173

[58] Field of Search .................. 514/105, 184, 514/461, 473; 549/472; 556/76, 18, 30, 70; 558/81, 82, 155, 173

[56] References Cited

U.S. PATENT DOCUMENTS 4,177,216  12/1979  Doorakian ..................... 260/606.5
4,177,716  12/1979  Doorakian ..................... 260/606.5 F

FOREIGN PATENT DOCUMENTS 4029747  4/1991  Germany.
3942933  6/1991  Germany.
4111105  10/1992  Germany.

*Primary Examiner*—Gollamudi S. Kishore
*Attorney, Agent, or Firm*—Cushman Darby & Cushman IP Group of Pillsbury Madison & Sutro LLP

[57] ABSTRACT

Phospholipid derivatives containing higher elements of the Vth main group (P, As, Sb, Bi), their method of preparation and antineoplastic and antimicrobially active medications that can be prepared from the phospholipid derivatives.

1 Claim, No Drawings

PHOSPHOLIPID DERIVATIVES CONTAINING HIGHER ELEMENTS OF THE FIFTH GROUP

This is a division of application Ser. No. 08/124,492, filed Sep. 22, 1993, now U.S. Pat. No. 5,449,798.

The present invention relates to novel compounds which may be used in tumor therapy and for the treatment of skin and auto-immune diseases.

BACKGROUND OF THE INVENTION

Long-chain alkylphosphocholines with an antimicrobial action are described by Kanetani et al., Nippon Kayaku Kaishi, 9, 1452 (1984).

European patent application 108 565 (applicant: Takeda) relates to compounds of the general formula $$R^1(O)_n-\overset{O}{\underset{O^-}{\overset{\|}{P}}}-OCH_2CH_2\overset{+}{N}\overset{R^2}{\underset{R^4}{\diagdown}}R^3$$

in which $R^1$ is an aliphatic hydrocarbon radical with 8–30 carbon atoms, the radicals $R^2$, $R^2$ and $R^2$ are the same or different or hydrogen or lower alkyl radicals or where the group $NR^2R^3R^4$ represents a cyclic ammonium group and n has the value 0 or 1. These compounds are stated to have an anti-tumour effect and a fungus-inhibiting effect.

SUMMARY OF THE INVENTION

The compounds of the invention may be used in tumour therapy and for the treatment of skin and auto-immune diseases, in particular the compounds of Formula I, $$R^5-X-A-\overset{O}{\underset{\underline{|O|^-}}{\overset{\|}{P}}}-O-A_1-R^6 \quad \text{Formula I}$$

where $R^5$ represents a straight-chain or branched alkyl radical with 10–24 carbon atoms which may also contain one to three double or triple bonds, A represents a simple bond or one of the groups with the formulae II–VI $$-CH_2-CH_2-CH_2-O- \quad (II)$$

$$-CH_2-CH_2-O- \quad (III)$$

$$-CH_2-\underset{OR^7}{\overset{|}{CH}}-CH_2-O- \quad (IV)$$

$$\underset{CH_2-OR^7}{\overset{CH_2-CH-O-}{|}} \quad (V)$$

$$\underset{H_2C}{\overset{CH_2}{\diagdown}}\underset{CH_2}{\overset{CH-O-}{\diagup}}O \quad (VI)$$

where $R^7$ represents a straight chain alkyl group with 1 to 4 carbon atoms which may also be branched.

The groups (II) to (VI) are so oriented that the oxygen atom is bound to the phosphorus atom of the compound of Formula I.

X=oxygen or sulfur atom or NH, when A=single bond

X=oxygen or sulphur atom when A is a compound of the groups of formulae (II) to (VI)

$A_1$=straight-chain or branched alkyl radical with 2 to 10 carbon atoms which may also be unsaturated and can be substituted by halogen or hydroxy groups.

$R^6=^{(+)}YR^8R^9R^{10}$ with $R^8-R^{10}$=straight chain, branched or cyclic alkyl radicals with 1 to 6 carbon atoms, which may be the same or different, or hydrogen Y=P, As, Sb or Bi, or a group of formula VII $$\underset{H_2C}{\overset{R^8}{\underset{\diagdown}{\overset{|}{-Y^+-(CH_2)_n}}}}\underset{CH_2-W}{\overset{CH_2}{\diagup}} \quad (VII)$$

with n=0 or 1

W=$CH_2$, O, NH or S; provided n=1, if W is not equal to $CH_2$. where Y has the meanings P, As and Sb.

The compounds of formula I with Y=As and Sb are for example suitable for the treatment of protozoal diseases. All compounds are, moreover, particularly suitable as agents against tumor diseases.

The compounds of the invention are suitable for the treatment of blood disorders, such as of anemias as can occur in combination with tumor diseases. In addition, the compounds of the invention may be used for the treatment of diseases of the bone system, for example osteoporosis.

In addition, the compounds of Formula I may be used for the treatment of virus disorders and bacterial infections.

The compounds are characterised by low toxicity.

The compound according to Example 3 thus has an $LD_{50}$ on single administration per os in the mouse of more than 1470 mg/kg body weight.

Preparation:

The following are procedures for the preparation of the compounds of the invention:

Process 1

The first step of the single pot process consists in the reaction of phosphorus oxychloride with alcohol, thioalcohol or amine in halogenated hydrocarbons, saturated cyclic ethers, acyclic ethers, saturated hydrocarbons with 5 to 10 carbon atoms, liquid aromatic hydrocarbons which may also be substituted by halogen (in particular chlorine) or in mixtures of the above mentioned solvents or without solvents, optionally in the presence of a conventional base substance. Halogenated hydrocarbons that may for example be considered are hydrocarbons with 1 to 6 carbon atoms, where one or several or all hydrogen atoms are replaced by chlorine atoms. Methylene chloride, chloroform, ethylene chloride, chlorobenzene, dichlorobenzene may for example be used. If halogen-substituted aromatic hydrocarbons are used, these are preferably substituted by one or two halogen atoms.

Saturated cyclic ethers that may for example be used are ethers with a ring size of 5–6 which consist of carbon atoms and one or two oxygen atoms.

Examples thereof are tetrahydrofuran, dioxane.

The acyclic ethers consist of 2 to 8 carbon atoms and are liquid. The following may for example be used: diethyl ether, diisobutyl ether, methyl-tert.-butyl ether, diisopropyl ether.

Saturated hydrocarbons that may be used are unbranched and branched hydrocarbons that consist of 5 to 10 carbon atoms and are liquid. Examples are pentane, hexane, heptane, cyclohexane.

Aromatic hydrocarbons that may for example be considered are benzene and alkyl-substituted benzenes, the alkyl substituents containing 1 to 5 carbon atoms.

Base substances that may be considered both for the reaction of the phosphorus oxychloride with the alcohol, thioalcohol or amine and also for the subsequent reaction with the phosphonium, stibonium or bismuthonium salt are amines, for example aliphatic amines of the formula $NR^7R^8R^9$, where $R^7$, $R^8$ and $R^9$ are the same or different and represent hydrogen or $C_1$–$C_6$-alkyl or also aromatic amines such as pyridine or picoline. Furthermore it is also possible to use quinoline, diisopropylamine, isoquinoline, triethylamine, Hünigs Base (Hünig, Kissel, Chem. Ber., 91 (380) 1958).

During the reaction with the phosphonium, stibonium or bismuthonium salt the base substance required for this purpose may be added at the same time or also before the phosphonium, stibonium or bismuthonium salt. A solvent is required for this reaction in any event; this means that if the first step of the reaction occurs without a special solvent, a solvent has to be added at this stage.

The Mol ratio of phosphorus oxychloride to alcohol, thioalcohol or amine is for example between 1.5:1 and 0.8:1.

If the reaction of the phosphorus oxychloride with the alkanol or thioalkanol or the amine occurs in the presence of a base substance, the amount of base substance is for example 1 to 3 mol for each Mol $POCl_3$.

For the subsequent reaction with the phosphonium, stibonium or bismuthonium salt, the amount of base substance used is for example 1 to 5 Mol for each Mol of alcohol, thioalcohol or amine.

The reaction temperature of the reaction of phosphorus oxychloride with alcohol, thioalcohol or amine with the amine is between −30° C. and +30° C., preferably −15° C. and 0° C., in particular −10° C. and 0° C. The reaction time of this reaction is for example 0.5–5 hours, preferably 1–3 hours, in particular 1.5–2 hours. If the reaction occurs in the presence of a base, it generally occurs quickly (about 30 minutes).

The product obtained is reacted, without isolation and purification, in an inert solvent with a phosphonium, arsonium, stibonium or bismuthonium salt of Formula VIII

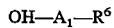   Formula VIII where $A_1$ and $R^6$ have the meanings given above.

Arsenocholine and its salts can for example be prepared according to the instructions set out in K. Irgolic, Applied Organometallic Chemistry (1987) 1, p. 403–412.

The phosphonium, stibonium or bismuthonium salt is added thereafter in portions or all at once.

In accordance therewith, salts with mineral acids (such as sulphuric acid, hydrochloric acid) as well as salts with organic acids such as acetic acid, para-toluenesulfonic acid and the like may be used as salts of the phosphonium, stibonium or bismuthonium salt.

This reaction step occurs in an inert solvent. The solvents that may be considered for this step are the same as those used for the reaction of phosphorus oxychloride with alcohol, thioalcohol or amine if this reaction occurs in a solvent.

The base substance is then dissolved in one of the solvents mentioned, or added dropwise without solvent.

The solvents used for the base substance in this case are preferably: halogenated hydrocarbons, saturated cyclic ethers, acyclic ethers, saturated hydrocarbons with 5 to 10 carbon atoms, liquid aromatic hydrocarbons or mixtures of the above mentioned solvents.

These are the same solvents as can be used for reacting phosphorus oxychloride with alcohol, thioalcohol or amine.

Addition of the base substance increases the temperature. Care is taken to ensure that the temperature is maintained within a range between 0° C. to 40° C., preferably 10° C. to 30° C., in particular 15° C. to 20° C.

The reaction mixture is then stirred at 5° C. to 30° C., preferably 15° C. to 25° C., (for example for 1 hour to 40 hours, preferably 3 hours to 15 hours).

The reaction batch is hydrolyzed by adding water, during which the temperature should be maintained between 10° C. and 30° C., preferably 15° C. and 30° C., in particular between 15° C. and 20° C.

The previously mentioned hydrolysis liquids can also contain base substances. Base substances of this type that may be considered are carbonates and hydrogen carbonates of alkali and alkaline earth metals.

To complete the hydrolysis, stirring is then continued for a further 0.5 hours to 4 hours, preferably 1 to 3 hours, in particular 1.5 to 2.5 hours at 10° C. to 30° C., preferably at 15° C. to 25° C., in particular at 18° C. to 22° C.

The reaction solution is then washed with a mixture of water and alcohols (preferably aliphatic saturated alcohols with 1 to 4 carbon atoms), which may optionally still contain a base.

The mixing ratio water:alcohol can for example be between 5 and 0.5, preferably 1–3 (V/V).

Bases which may for example be considered for the washing liquid are carbonates and hydrogen carbonates of alkali and alkaline earth metals as well as ammonia (for example aqueous ammonia). A 3% sodium carbonate solution in water is particularly preferred.

The reaction solution may then optionally be washed with an acid solution.

The acid washing is advantageous for removing unreacted base portions of the reaction solution, particularly when methylene chloride is used as solvent.

The washing solution consists of a mixture of water and alcohols. Mixtures of aliphatically saturated alcohols with 1 to 4 carbon atoms may preferably be considered. Optionally it is possible for an acid substance to be present. The mixing ratio water:alcohol can for example be between 5 and 0.5, preferably 1–3 (V/V).

Mineral acids and organic acids may for example be considered as acid substance for the washing liquid, for example hydrochloric acid, sulphuric acid or tartaric acid and citric acid. A 10% solution of hydrochloric acid in water is particularly preferred.

The resulting product is then washed once more with a mixture of water and alcohols. Mixtures of aliphatic saturated rated alcohols with 1 to 4 carbon atoms may preferably be considered, it optionally also being possible for a base substance to be present as well.

The mixing ratio water:alcohol can for example be between 5 and 0.5, preferably 1–3.

The washed phases are then combined and dried in conventional manner, the solvent then being removed (preferably under reduced pressure, for example 5 to 100 hPascal), optionally after addition of 150–1000 ml, preferably 300–700 ml, in particular 450–550 ml of an aliphatic alcohol (for each Mol part by weight of dry product).

Alcohols that may be considered are preferably saturated aliphatic alcohols with a chain length of 1 and 5 carbon atoms. Particularly preferred alcohols in this case are n-butanol, isopropanol. This alcohol treatment is intended to totally remove residual water. The product so obtained can be purified in the conventional manner (for example by chromatography, recrystallisation).

Process 2 consists of the reaction of a cyclic phosphoric acid triester ester with a compound of formula X or XI.

The cyclic phosphoric acid ester is obtained according to EP 108 565 by reacting the cyclic phosphoric acid diester chloride with the alkanol.

A compound of formula IX

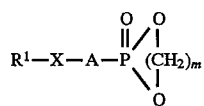

where m=2 or 3, is reacted with a compound of formula (X) or (XI) YR$^6$R$^7$R$^8$

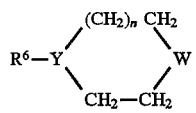

(other meanings, see formula I) in an inert solvent at increased temperature.

Inert solvents that may be considered are aliphatic nitriles, for example acetonitrile, propionitrile, and also polar solvents such as N-methylpyrrolidone, dimethylformamide, dimethylacetamide.

The reaction temperature is between 30° C. and 140° C., preferably between 50° C. and 120° C., quite particularly between 70° C. and 100° C.

This reaction may be carried out both at atmospheric pressure and also at elevated pressure. The pressure is between 1000 hPa and 2000 hPa, preferably between 1000 hPa and 1750 hPa and, quite particularly preferred, between 1000 hPa and 1500 hPa.

The reaction time is between 0.5 hours and 4 hours; if the reaction is carried out under elevated pressure, the time is for example 2 hours at 1500 hPa and 85° C.

Process 3

Reaction of activated derivatives of the phosphoric acid esters

This process consists of the reaction of hydrogen phosphate with compounds of the General Formula XIII

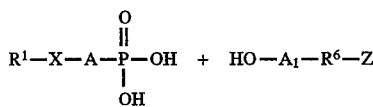

In formula XIII, R$^1$ X, A, A$_1$ and R$^6$ have the meanings given earlier,

Z=represents a group according to formulae X or XII.

HO in the formula for the hydrogen phosphate can be replaced by halide, tosylate, mesylate and triflate.

Carbodiimides such as dicyclohexylcarbodiimide may be used as desiccating agents in the condensation reaction.

Aprotic, polar solvents such as acetonitrile, dimethylformamide, dimethylacetamide, dimethylsulfoxide, N-methyl-pyrrolidone and chlorinated hydrocarbons may be considered as solvents for the variant of the process.

The temperature is for example 20°–80° C., 40°–60° C. being particularly preferred. The reaction time is for example 4 hours.

Process 4

A compound of the general formula XII which represents an activated phosphoric acid ester at the aliphatic radical

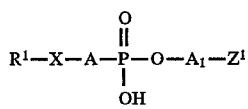

where Z$^1$=chlorine, bromine, mesylate (XII), tosylate or iodine (other meanings as before) is reacted with a compound of formulae (X) or (XI).

This reaction occurs in known manner without solvents or in an inert solvent at temperatures between 50° C. and 150° C.

The solvents that may be considered are the same as for Process 2.

The reaction is followed by conversion with acid-binding or halogen-binding substances such as Ag$_2$CO$_3$ and with bases, for example with alkali metal carbonates and alkaline earth metal carbonates and organic amines. Solvents may be aliphatic alcohols, for example methanol, ethanol and isopropanol. This step may also be at elevated temperature.

The exclusion of moisture and atmospheric oxygen, conventional in the metal organic field, should be observed before all reactions are completed.

Purification:

The purification process may follow all 4 processes. The above described compound may be purified by dissolving the residue formed after evaporation of the reaction medium, optionally under reduced pressure in an organic solvent (preferably lower alcohols with a water content of 0–4%, such as methanol, ethanol, isopropanol, n-butanol) and treating with mixed bed ion exchangers or successively with acid and base ion exchangers. The filtrate obtained is then stirred with a mixed bed ion exchanger, for example Amberlite® MB3, for example for 1 to 5 hours, preferably 2 hours, at 10° C. to 50° C., preferably 20° C. Instead of a mixed bed ion exchanger, purification may also be carried out successively with an acid ion exchanger and a base ion exchanger.

All insoluble solids containing ion exchanging groups may be used as ion exchangers.

Acid ion exchangers are those which for example contain acid groups such as sulfonic acid groups, carboxyl groups. Examples are ion exchangers with sulfonic acid groups in a polystyrene matrix, such as Amberlite® IR 120, Dowex® HCR, Duolite® C 20 or Lewatit® S 100. Weakly acidic ion exchangers are for example those which carry carboxylic acid groups on the basis of a polyacrylic acid matrix, such as Amberlite® IRC 76, Duolite® C 433 or Relite® CC.

Base ion exchangers that may for example be considered are those having primary, secondary, tertiary or quaternary amino groups on a polymer matrix (for example polystyrene matrix), such as Duolite® A 101, Duolite® A 102, Duolite® A 348, Duolite® A 365, Duolite® A 375, Amberlite® IRA 67, Duolite® A 375, Amberlite® IRA 458 and Duolite® A 132.

Mixed bed ion exchangers are mixtures of acid and alkaline ion exchanger resins, such as Amberlite® MB1, Amberlite® MB2, Amberlite® MB3 and Amberlite® MB6.

Reference is further made to Ullmann's Encyclopedia of Industrial Chemistry, 5th Edition (1989), Volume A14, p. 450 which describes all commercially conventional ion exchangers which may be used in the purification process.

After the removal of the ion exchanger resin, evaporation is effected at 40° C. to 70° C. under reduced pressure (for example 20 Torr to 200 Torr) and followed by recrystallisation from halogenated hydrocarbons, saturated aliphatic ketones, alcohol/ketone mixtures or from saturated or aromatic hydrocarbons.

Halogenated hydrocarbons that may be considered for the recrystallisation are for example hydrocarbons with 1 to 6 carbon atoms, one or several or all hydrogen atoms being replaced by chlorine atoms.

Methylene chloride, chloroform, ethylene chloride, chlorobenzene may for example be used.

The alcohols may be saturated aliphatic alcohols with 1 to 6 carbon atoms and 1 to 3 hydroxyl groups. Ketones may be saturated, aliphatic ketones with 3 to 6 carbon atoms. The mixing ratio alcohol:ketone is 1 to 1–5 (volume/volume).

An ethanol/acetone mixture in the ratio 1:1 (V/V) is particularly preferred.

Saturated or aromatic hydrocarbons may be considered: high-boiling point petroleum ether, toluene, xylene, ethyl benzene.

The compounds of the invention according to formula (I) are characterised by low toxicity with a good anti-tumor effect.

The compound according to Example 1 has for example an $EC_{90}$ of 2.9 µg/ml in the L1210-cell culture experiment.

The $EC_{90}$ is the concentration of an anti-tumor substance stance in µg/ml which inhibits the growth of cancer cells by 90% in vitro compared to a control experiment without addition of the anti-tumor substance.

DETAILED DESCRIPTION OF PREFERRED EMBODIMENTS

The following examples illustrate the invention.

EXAMPLE 1

IUPAC name

2-[[(Octadecyloxy)hydroxyphosphenyl]oxy]-As,As,As-trimethyl-ethyl arsonium inner salt $$H_{37}C_{18}O-\underset{\underset{O^-}{|}}{\overset{\overset{O}{\|}}{P}}-O-(CH_2)_2-\overset{+}{As}(CH_3)_3 \quad C_{23}H_{50}AsO_4P(496,54)$$

2.3 ml (25 mmol) Phosphorous oxychloride are dissolved in 15 ml chloroform and reacted at 0° C.–5° C. dropwise with a solution of 6.1 g (22.5 mmol) octadecanol in 25 ml chloroform containing 8 ml pyridine. Duration of addition: 30 min to 1 hour. The mixture is stirred for a further hour at room temperature and 7.4 g (30 mmol) arsenocholine bromide is then added thereto in one portion. 10 ml Pyridine are added dropwise to this solution so that the temperature does not exceed 20° C.–25° C. When addition is completed the mixture is stirred for a further 3 hours at room temperature, hydrolized after cooling to 5° C. to 10° C. with 4 ml water ter and washed with, in each case, 20 ml water/methanol (1:1), 3 percent sodium carbonate/methanol (1:1), 3 percent citric acid/methanol (1:1) and finally water/methanol (1:1). The organic phase is dried over magnesium sulphate, concentrated and the residue taken up in 96 percent ethanol. After filtration the mixture is stirred with 30 g ion exchanger Amberlite® MB 3. The result is sucked off via kieselguhr/active charcoal, concentrated in a vacuum and allowed to crystallize under acetone.

Yield: 2.54 g (23%)

| Elementary analysis: | C | H | As |
|---|---|---|---|
| calc. | 55.64% | 10.15% | 15.09% |
| found | 55.71% | 10.41% | 14.1% |
|  | 55.93% | 10.58% |  |

Thin layer chromatogram:
(chloroform/methanol/1M sodium acetate in 25 percent ammonia 70:40:10) RF=0.53.

EXAMPLE 2

IUPAC name

2-[[(hexadecyloxy)hydroxyphosphenyl]oxy]-As,As,As-trimethyl-ethyl arsonium inner salt $$H_{33}C_{16}O-\underset{\underset{O^-}{|}}{\overset{\overset{O}{\|}}{P}}-O-(CH_2)_2-\overset{+}{As}(CH_3)_3 \quad C_{21}H_{46}AsO_4P(496,48)$$

Preparation of this compound is carried out by analogy with Example 1 from 2.3 ml (25 mmol) phosphorous oxychloride, 5.5 g (22.5 mmol) hexadecanol, 8+10 ml pyridine and 7.4 g (30 mmol) arsenocholine bromide. Purification by treatment with 23 g ion exchanger Amberlite® MB3 in 96 percent ethanol.

Yield: 1.4 g (13%)

| Elementary analysis: | C | H |
|---|---|---|
| calc. | 53.84% | 9.90% |
| found | 53.45% | 10.16% |
|  | 53.67% | 10.20% |

Thin layer chromatogram:
(chloroform/methanol/1M sodium acetate in 25 percent ammonia 70:40:10) RF=0.48.

EXAMPLE 3

IUPAC name

2-[[(cis-13-docosenyloxy)hydroxyphosphenyl]oxy]-As,As,As-trimethyl-ethyl arsonium inner salt $$\text{cis-}\Delta^{13}\text{-}C_{22}H_{43}O-\underset{\underset{O^\ominus}{|}}{\overset{\overset{O}{\|}}{P}}-O-(CH_2)_2-As^{\oplus}(CH_3)_3 \quad C_{27}H_{56}AsO_4P \quad (550,63)$$

x H₂O

Preparation is carried out by analogy with Example 1 from 2.3 ml (25 mmol) phosphorous oxychloride, 7.3 g (22.5 mmol) erucyl alcohol, 8+10 ml pyridine and 7.4 g (30 mmol) arsenocholine bromide. Purification by treatment with 23 ion exchanger Amberlite® MB3 in 96 percent ethanol.

Yield: 1.1 g (10%)

| Elementary analysis: | C | H |
|---|---|---|
| calc. | 55.28% | 10.31% |
| found | 54.98% | 10.19% |
|  | 55.08% | 10.30% |

Thin layer chromatogram:
(chloroform/methanol/1M sodium acetate in 25 percent ammonia 70:40:10) RF=0.52.

EXAMPLE 4

IUPAC name

2-[[(Octadecyloxy)hydroxyphosphenyl]oxy]-P,P,P-trimethyl-ethyl phosphonium inner salt $$H_{37}C_{18}O-\underset{\underset{O^-}{|}}{\overset{\overset{O}{\|}}{P}}-O-(CH_2)_2\overset{+}{P}(CH_3)_3 \quad C_{23}H_{50}P_2O_4(452.59)$$

Preparation was carried out by analogy with Example 1 from 4.6 ml (50 mmol) phosphorous oxychloride, 12.2 g (45 mmol) octadecanol, 16+20 ml pyridine and 12.1 g (60 mmol) phosphocholine bromide. Purification was by treatment with 50 g ion exchanger Amberlite^R MB3 in 96 percent ethanol.
Yield: 2.1 g (10%)

| Elementary analysis: | C | H |
|---|---|---|
| calc. | 60.04% | 11.14% |
| found | 60.94% | 11.53% |
|  | 60.44% | 11.42% |

Thin layer chromatogram:
(chloroform/methanol/1M sodium acetate in 25 percent ammonia 70:40:10) RF=0.43.

EXAMPLE 5

2-[[(Hexadecyloxy)hydroxyphosphenyl]oxy]-P,P,P-trimethyl-ethyl phosphonium inner salt

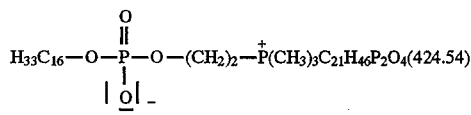

Preparation was carried out by analogy with Example 1 from 4.6 ml (50 mmol) phosphorous oxychloride, 10.9 g (45 mmol) hexadecanol, 16+20 ml pyridine and 12.1 g (60 mmol) phosphocholine bromide. Purification by treatment with ion exchanger Amberlite® MB3 in 96 percent ethanol.
Yield: 5.2 g (27%)

| Elementary analysis: | C | H |
|---|---|---|
| calc. | 59.41% | 10.92% |
| found | 58.73% | 11.16% |
|  | 59.19% | 12.02% |

RF=0.47
Thin layer chromatogram:
(chloroform/methanol/1M sodium acetate in 25 percent ammonia 70:40:10) RF=0.43.

EXAMPLE 6

2-[[(Cis-13-docosenyloxy)hydroxyphosphenyl]oxy]-P,P,P-trimethylethyl phosphonium inner salt

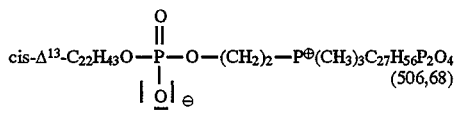

x H$_2$O

Preparation by.analogy with Example 1 from 3.5 ml (38 mmol) phosphorous oxychloride, 11.2 g (34 mmol) erucyl alcohol, 12+15 ml pyridine and 9.2 g (46 mmol) phosphocholine bromide. Purification by treatment with 45 g ion exchanger Amberlite® MB3 in 96 percent ethanol.
Yield: 1.9 g (11%)

| Elementary analysis: | C | H |
|---|---|---|
| calc. | 60.75% | 11.14% |
| found | 60.56% | 11.35% |
|  | 61.39% | 11.54% |

Thin layer chromatogram:
(chloroform/methanol/1M sodium acetate in 25 percent ammonia 70:40:10) RF=0.47.

EXAMPLE 7

2-[[(Octadecyloxy)hydroxyphosphenyl]oxy]-As,As,As-trimethyl-ethyl arsonium inner salt

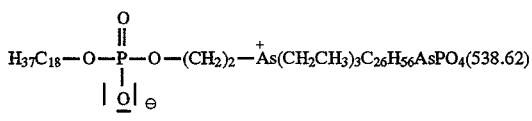

x 2 H$_2$O

Preparation by analogy with Example 1 from 3.5 ml (38 mmol) phosphorous oxychloride, 9.33 g (35 mmol) octadecanol, 12+15 ml pyridine and 13.2 g (46 mmol) triethyl-(2-hydroxyethyl)-arsonium bromide. Purification by treatment with ion exchanger Amberlite® MB3 in 96 percent ethanol and subsequent column chromatography on silica gel with CH$_2$Cl$_2$/CH$_3$OH/25 percent ammonia 70:40:10.
Yield: 3.59 g (18%)

| Elementary analysis: | C | H |
|---|---|---|
| calc. | 54.35% | 10.52% |
| found | 54.65% | 11.58% |
|  | 54.41% | 11.78% |

Thin layer chromatogram:
(chloroform/methanol/25 percent ammonia 80:25:5).

EXAMPLE 8

2-[[(Hexadecyloxy)hydroxyphosphenyl]oxy]-As,As,As-triethylethyl arsonium inner salt

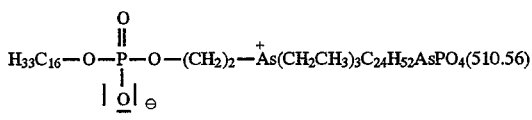

x 3 H$_2$O

Preparation by analogy with Example 1 from 3.5 ml (38 mmol) phosphorous oxychloride 8.43 g (35 mmol) hexadecanol, 12+15 ml pyridine and 13.2 g (46 mmol) trimethyl-ethyl (2-hydroxyethyl) arsonium bromide. Purification by treatment with ion exchanger Amberlite® MB3 in 96 percent ethanol and subsequent column chromatography on silica gel with CH$_2$Cl$_2$/CH$_3$OH/25 percent ammonia 70:40:10.
Yield: 2.26 g (13%)

| Elementary analysis: | C | H |
|---|---|---|
| calc. | 51.05% | 10.35% |
| found | 50.22% | 11.37% |
|  | 50.81% | 11.77% |

R$_F$=0.57
Thin layer chromatogram:
(chloroform/methanol/25 percent ammonia 80:25:5).

EXAMPLE 9

2-[[(Cis-13-docosenyloxy)hydroxyphosphenyl]oxy]-As,As,As-ethylethyl arsonium inner salt $$\text{cis-}\Delta^{13}\text{-}C_{22}H_{43}O-\underset{\underset{\ominus}{|\underline{O}|}}{\overset{\overset{O}{\|}}{P}}-O-(CH_2)_2-\overset{+}{As}(CH_2CH_3)_3 \quad C_{30}H_{62}AsPO_4(552,71)$$

x 3 H$_2$O

Preparation by analogy with Example 1 from 3.5 ml (38 mmol) phosphorous oxychloride 11.4 g (35 mmol) erucyl alcohol, 12+15 ml pyridine and 13.2 g (46 mmol) trimethyl-(2-hydroxyethyl) arsonium bromide. Purification by treatment with 30 g ion exchanger Amberlite® MB3 in 96 percent ethanol and subsequent column chromatography on silica gel with CH$_2$Cl$_2$/CH$_3$OH/25 percent ammonia 70:40:10.

Yield: 4.50 g (22%)

| Elementary analysis: | C | H |
|---|---|---|
| calc. | 51.05% | 10.35% |
| found | 50.22% | 11.37% |
|  | 50.81% | 11.77% |

R$_f$=0.57

Thin layer chromatogram:

(chloroform/methanol/25 percent ammonia 80:25:5).

EXAMPLE 10

3-[[(Octadecyloxy)hydroxyphosphenyl]oxy]-As,As,As-trimethyl propylarsonium inner salt $$H_{37}C_{18}-O-\underset{\underset{\ominus}{|\underline{O}|}}{\overset{\overset{O}{\|}}{P}}-O-(CH_2)_3-\overset{+}{As}(CH_3)_3 \quad C_{24}H_{52}AsPO_4(510,56)$$

x 2 H$_2$O

Preparation by analogy with Example 1 from 4.0 ml (38 mmol) phosphorous oxychloride 10.8 g (35 mmol) octadecanol, 14+17 ml pyridine and 13.2 g (53 mmol) trimethyl-2-hydroxyethyl arsonium bromide. Purification by treatment with 30 g ion exchanger Amberlite® MB3 in 96 percent ethanol and subsequent column chromatography on silica gel with CH$_2$Cl$_2$/CH$_3$OH/25 percent ammonia 70:40:10.

Yield: 1.97 g (10%)

| Elementary analysis: | C | H |
|---|---|---|
| calc. | 52.74% | 10.33% |
| found | 52.22% | 10.38% |
|  | 52.19% | 10.37% |

R$_f$=0.47

Thin layer chromatogram:

(chloroform/methanol/25 percent ammonia 70: 40: 10).

EXAMPLE 11

3-[[(Hexadecyloxy)hydroxyphosphenyl]oxy]-As,As,As-trimethyl propylarsonium inner salt $$H_{33}C_{16}-O-\underset{\underset{\ominus}{|\underline{O}|}}{\overset{\overset{O}{\|}}{P}}-O-(CH_2)_3-\overset{+}{As}(CH_3)_3 \quad C_{22}H_{48}AsPO_4(482.51)$$

15 x 5 H$_2$O

Preparation by analogy with Example 1 from 4.0 ml (43 mmol) phosphorous oxychloride 9.7 g (40 mmol) hexadecanol, 14+17 ml pyridine and 13.6 g (53 mmol) trimethyl-(3-hydroxypropyl) arsonium bromide. Purification by treatment with 30 g ion exchanger Amberlite® MB3 in 96 percent ethanol and subsequent column chromatography on silica gel with CH$_2$Cl$_2$/CH$_3$OH/25 percent ammonia 70:40:10.

Yield: 2.0 g (10%)

| Elementary analysis: | C | H |
|---|---|---|
| calc. | 51.86% | 10.09% |
| found | 51.55% | 10.05% |
|  | 51.74% | 10.17% |

R$_f$=0.47

Thin layer chromatogram:

(chloroform/methanol/25 percent ammonia 70:40:10).

EXAMPLE 12

3-[[(Cis-13-docosenyloxy)hydroxyphosphenyl]oxy]-As,As,As-trimethylpropyl arsonium inner salt $$\text{Cis-}\Delta^{13}\text{-}C_{22}H_{43}O-\underset{\underset{\ominus}{|\underline{O}|}}{\overset{\overset{O}{\|}}{P}}-O-(CH_2)_3-\overset{+}{As}(CH_3)_3 \quad C_{28}H_{58}AsPO_4(564,66)$$

x 3 H$_2$O

Preparation by analogy with Example 1 from 4.0 ml (43 mmol) phosphorous oxychloride 13.0 g (40 mmol) erucyl alcohol, 14+17 ml pyridine and 13.2 g (53 mmol) trimethyl-(3-hydroxyproply) arsonium bromide. Purification by treatment with 30 g ion exchanger Amberlite® MB3 in 96 percent ethanol and subsequent column chromatography on silica gel with CH$_2$Cl$_2$/CH$_3$OH/25 percent ammonia 70:40:10.

Yield: 2.4 g (11%)

| Elementary analysis: | C | H |
|---|---|---|
| calc. | 54.36% | 10.43% |
| found | 54.45% | 10.34% |
|  | 54.86% | 10.51% |

R$_f$=0.50

Thin layer chromatogram:

(chloroform/methanol/25 percent ammonia 70:40:10).

EXAMPLE 13

3-[[(Cis-13-docosenyloxy)hydroxyphosphenyl]oxy]-P,P,P-tri-methylpropyl phosphonium inner salt

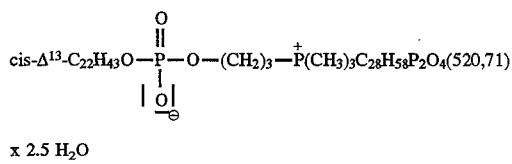

x 2.5 H₂O

Preparation by analogy with Example 1 from 4.2 ml (45 mmol) phosphorous oxychloride 13.8 g (42 mmol) erucyl alcohol, 14+18 ml pyridine and 12.0 g (56 mmol) trimethyl-(3-hydroxypropyl) arsonium bromide. Purification by treatment with 45 g ion exchanger Amberlite® MB3 in 96 percent ethanol and subsequent column chromatography on silica gel with $CH_2Cl_2/CH_3OH/25$ percent ammonia 70:40:10.

Yield: 2.93 g (13%)

| Elementary analysis: | C | H |
|---|---|---|
| calc. | 59.44% | 11.22% |
| found | 59.28% | 10.92% |
|  | 59.57% | 11.54% |

$R_F$=0.25

Thin layer chromatogram:
(chloroform/methanol/(1M sodium acetate in 25 percent ammonia 70:40:10).

EXAMPLE 14

3-[[(Octadecyloxy)hydroxyphosphenyl]oxy]-P,P,P-trimethylpropyl phosphonium inner salt

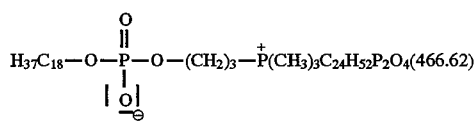

x 1.5 H₂O

Preparation by analogy with Example 1 from 4.2 ml (45 mmol) phosphorous oxychloride 11.4 g (42 mmol) octadecanol, 14+18 ml pyridine and 12.2 g (56 mmol) trimethyl-(3-hydroxypropyl) phosphonium bromide. Purification by treatment with 55 g ion exchanger Amberlite® MB3 in 96 percent ethanol and subsequent column chromatography on silica gel with $CH_2Cl_2/CH_3OH/25$ percent ammonia 70:40:10.

Yield: 2.27 g (11%)

| Elementary analysis: | C | H |
|---|---|---|
| calc. | 58.39% | 11.23% |
| found | 59.08% | 11.42% |
|  | 58.63% | 11.39% |

$R_F$=0.50

Thin layer chromatogram:
(chloroform/methanol/1M sodium acetate in 25 percent ammonia 70:40:10).

EXAMPLE 15

3-[[(Hexadecyloxy)hydroxyphosphenyl]oxy]-P,P,P-trimethylpropyl phosphonium inner salt

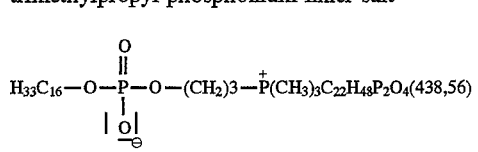

x H₂O

Preparation by analogy with Example 1 from 4.2 ml (45 mmol) phosphorous oxychloride 10.2 g (42 mmol) hexadecanol, 14+18 ml pyridine and 12.0 g (56 mmol) trimethyl-(3-hydroxypropyl) phosphonium bromide. Purification by treatment with 55 g ion exchanger Amberlite® MB3 in 96 percent ethanol and subsequent column chromatography on silica gel with $CH_2Cl_2/CH_3OH/25$ percent ammonia 70:40:10.

Yield: 1.86 g (10%)

| Elementary analysis: | C | H |
|---|---|---|
| calc. | 57.87% | 11.04% |
| found | 57.30% | 11.20% |
|  | 57.02% | 11.29% |

$R_F$=0.50

Thin layer chromatogram:
(chloroform/methanol/1M sodium acetate in 25 percent ammonia 70:40:10).

EXAMPLE 16

3-[[(Nonadecyloxy)hydroxyphosphenyl]oxy]-P,P,P-trimethyl-ethyl phosphonium inner salt

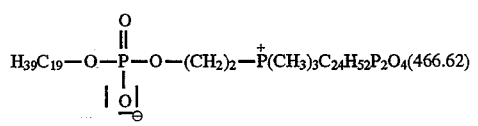

x 0.5 H₂O

Preparation by analogy with Example 1 from 3.2 ml (35 mmol) phosphorous oxychloride 9.18 g (32 mmol) nonadecanol, 11+14 ml pyridine and 8.64 g (43 mmol) phosphocholine bromide. Purification by treatment with 25 g ion exchanger Amberlite® MB3 in 96 percent ethanol and subsequent decocting twice with acetone.

Yield: 1.85 g (12%)

| Elementary analysis: | C | H |
|---|---|---|
| calc. | 60.61% | 11.23% |
| found | 60.69% | 11.55% |
|  | 61.01% | 11.39% |

$R_F$=0.58

Thin layer chromatogram:
(chloroform/methanol/(1M sodium acetate in 25 percent ammonia 70:40:10).

EXAMPLE 17

2-[[(Eicosyloxy)hydroxyphosphenyl]oxy]-P,P,P-trimethylethyl phosphonium inner salt

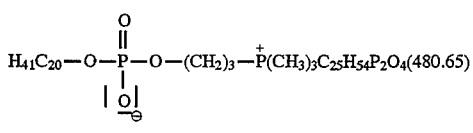

H₄₁C₂₀—O—P(=O)(O⁻)—O—(CH₂)₃—⁺P(CH₃)₃ C₂₅H₅₄P₂O₄(480.65)

x 0.5 H₂O

Preparation by analogy with Example 1 from 3.2 ml (35 mmol) phosphorous oxychloride 9.63 g (32 mmol) eicosanol, 11+14 ml pyridine and 8.64 g (43 mmol) phosphocholine bromide. Purification by treatment with 25 g ion exchanger Amberlite® MB3 in 96 percent ethanol and subsequent decocting twice in acetone.

Yield: 0.02 g (7%)

| Elementary analysis: | C | H |
|---|---|---|
| calc. | 61.32% | 11.32% |
| found | 61.72% | 11.65% |
|  | 61.55% | 11.47% |

$R_f = 0.53$

Thin layer chromatogram:

(chloroform/methanol/(1M sodium acetate in 25 percent ammonia 70:40:10).

EXAMPLE 18

2-[[(Nonadecyloxy)hydroxyphosphenyl]oxy]-As,As,As-trimethyl ethyl arsonium inner salt

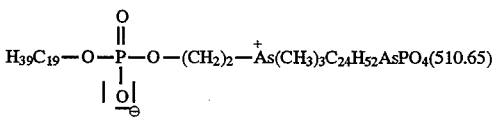

H₃₉C₁₉—O—P(=O)(O⁻)—O—(CH₂)₂—⁺As(CH₃)₃ C₂₄H₅₂AsPO₄(510.65)

x 0.5 H₂O

Preparation by analogy with Example 1 from 4.6 ml (50 mmol) phosphorous oxychloride 12.8 g (45 mmol) nonadecanol, 16+20 ml pyridine and 14.7 g (60 mmol) arsenocholine bromide. Purification by treatment with 55 g ion exchanger Amberlite® MB3 in 96 percent ethanol.

Yield: 4.05 g (18%)

| Elementary analysis: | C | H |
|---|---|---|
| calc. | 55.48% | 10.28% |
| found | 55.89% | 10.43% |
|  | 55.89% | 10.52% |

$R_f = 0.45$

Thin layer chromatogram:

(chloroform/methanol/25 percent ammonia 80:25:5).

EXAMPLE 19

2-[[(Eicosyloxy)hydroxyphosphenyl]oxy]-As,As,As-trimethyl-ethyl arsonium inner salt

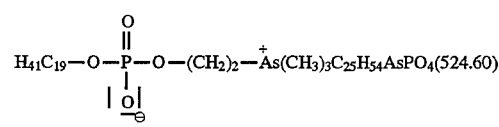

H₄₁C₁₉—O—P(=O)(O⁻)—O—(CH₂)₂—⁺As(CH₃)₃ C₂₅H₅₄AsPO₄(524.60)

Preparation by analogy with Example 1 from 4.6 ml (50 mmol) phosphorous oxychloride 13.4 g (45 mmol) eicosanol, 16+20 ml pyridine and 14.7 g (60 mmol) arsenocholine bromide. Purification by treatment with 50 g ion exchanger Amberlite® MB3 in 96 percent ethanol.

Yield: 2.81 g (12%)

| Elementary analysis: | C | H |
|---|---|---|
| calc. | 57.24% | 10.38% |
| found | 56.92% | 10.52% |
|  | 57.02% | 10.36% |

$R_f = 0.45$

Thin layer chromatogram:

(chloroform/methanol/25 percent ammonia 80:25:5).

EXAMPLE 20

2-[[(Heptadecyloxy)hydroxyphosphenyl]oxy]-As,As,As-trimethyl-ethyl arsonium inner salt

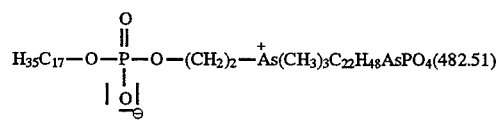

H₃₅C₁₇—O—P(=O)(O⁻)—O—(CH₂)₂—⁺As(CH₃)₃ C₂₂H₄₈AsPO₄(482.51)

x H₂O

Preparation by analogy with Example 1 from 4.6 ml (50 mmol) phosphorous oxychloride 11.5 g (45 mmol) heptadecanol, 16+20 ml pyridine and 14.7 g (60 mmol) arsenocholine bromide. mide. Purification by treatment with 35 g ion exchanger Amberlite® MB3 in 96 percent ethanol and subsequent stirring in acetone.

Yield: 1.20 g (6%)

| Elementary analysis: | C | H |
|---|---|---|
| calc. | 52.79% | 10.07% |
| found | 52.46% | 9.95% |
|  | 53.26% | 10.30% |

$R_f = 0.45$

Thin layer chromatogram:

(chloroform/methanol/1M sodium acetate in 25 percent ammonia 70:40:10).

EXAMPLE 21

2-[[(Octadecyloxy)hydroxyphosphenyl]oxy]-P,P-diethyl-p-yl-ethyl phosphonium inner salt

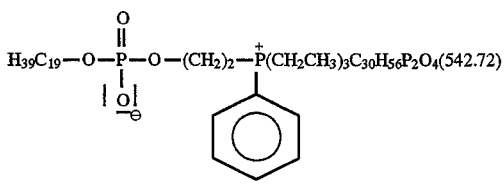

x H$_2$O

Preparation by analogy with Example 1 from 2.3 ml (25 mmol) phosphorous oxychloride 7.17 g (26.5 mmol) octadecanol, canol, 8+10 ml pyridine and 7.28 g (26.5 mmol) diethyl-(2-hydroxyethyl)-phenyl phosphonium bromide. Purification by treatment with 21 g ion exchanger Amberlite® MB3 in 96 percent ethanol and recrystallisation twice from acetone.

Yield: 1.76 g (13%)

| Elementary analysis: | C | H |
|---|---|---|
| calc. | 64.26% | 10.43% |
| found | 64.03% | 10.77% |
|  | 64.24% | 10.92% |

R$_F$32 0.37

Thin layer chromatogram:

(chloroform/methanol/25 percent ammonia 80:25:5).

EXAMPLE 22

2-[[(Cis-13-docosenyloxy)hydroxyphosphenyl]oxy]-P,P-diethyl P-phenyl-ethyl phosphonium inner salt

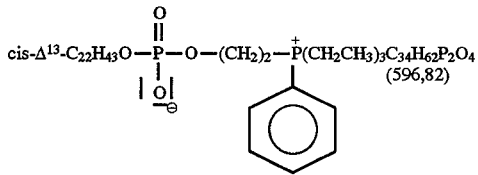

x 1.5 H$_2$O

Preparation by analogy with Example 1 from 2.3 ml (25 mmol) phosphorous oxychloride 8.6 g (27 mmol) erucyl alcohol, 8+10 ml pyridine and 7.28 g (27 mmol) diethyl-(2-hydroxyethyl)-phenyl phosphonium bromide. Purification by treatment with 30 g ion exchanger Amberlite® MB3 in 96 percent ethanol and crystallisation from acetone.

Yield: 2.53 g (17%)

| Elementary analysis: | C | H |
|---|---|---|
| calc. | 65.46% | 10.50% |
| found | 65.71% | 10.33% |
|  | 65.59% | 10.99% |

R$_F$=0.37

Thin layer chromatogram:

(chloroform/methanol/25 percent ammonia 80:25:5).

EXAMPLE 23

2-[[(4'-Dodecylcyclohexyl)methyloxy)hydroxyphosphenyl]oxy]-As,As,As-trimethylethyl arsonium inner salt

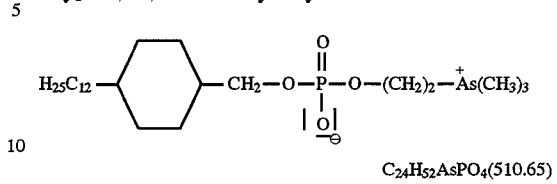

C$_{24}$H$_{52}$AsPO$_4$(510.65)

Preparation by analogy with Example 1 from 2.4 ml (26 mmol) phosphorous oxychloride 6.50 g (23 mmol) dodecylcyclohexyl methanol, 9+12 ml pyridine and 7.59 g (31 mmol) arsenocholine bromide. Purification by treatment with 30 g ion exchanger Amberlite® MB3 in 96 percent ethanol and stirring in acetone.

Yield: 1.64 g (14%)

| Elementary analysis: | C | H |
|---|---|---|
| calc. | 56.68% | 9.91% |
| found | 56.66% | 10.25% |
|  | 56.91% | 10.28% |

R$_F$=0.37

Thin layer chromatogram:

(chloroform/methanol/(1M sodium acetate in 25 percent ammonia 70:40:10).

EXAMPLE 24

1-0-Octadecyl-2-0-methyl-rac-glycerophosphoarsenocholine

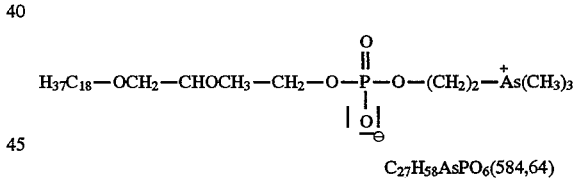

C$_{27}$H$_{58}$AsPO$_6$(584,64)

Preparation by analogy with Example 1 from 3.0 ml (33 mmol) phosphorous oxychloride 10.8 g (30 mmol) 1-0-Octadecyl-2-0-methyl-rac-glycerol 11+13 ml pyridine and 9.8 g (40 mmol) arsenocholine bromide. Purification by treatment with 55 g ion exchanger Amberlite® MB3 in 96 percent ethanol and stirring with acetone.

Yield: 5.83 g (33%)

| Elementary analysis: | C | H |
|---|---|---|
| calc. | 55.47% | 10.00% |
| found | 55.23% | 10.23% |
|  | 55.79% | 10.26% |

Thin layer chromatogram:

(chloroform/methanol/1M sodium acetate in 25 percent ammonia 70:40:10).

EXAMPLE 25

1-0-Octadecyl-2-0-methyl-rac-glycerophosphophosphocholine

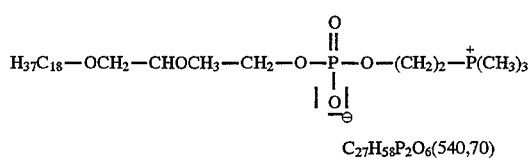

$C_{27}H_{58}P_2O_6 (540,70)$ x 0.5 H₂O

Preparation by analogy with Example 1 from 4.6 ml (50 mmol) phosphorous oxychloride 16.1 g (45 mmol) 1-0-Octadecyl-2-0-methyl-rac-glycerol 16+20 ml pyridine and 12.1 g (60 mmol) phosphocholine bromide. Purification by treatment with 45 g ion exchanger Amberlite® MB3 in 96 percent ethanol and stirring with acetone.
Yield: 6.25 g (26%)

| Elementary analysis: | C | H |
|---|---|---|
| calc. | 58.99% | 10.82% |
| found | 58.73% | 11.19% |
|  | 59.12% | 11.05% |

$R_F=0.52$
Thin layer chromatogram:
(chloroform/methanol/1M sodium acetate in 25 percent ammonia 70:40:10).

EXAMPLE 26

2-[[Octadecyloxy)hydroxyphosphenyl]oxy]-Sb, Sb, Sb-trimethyl-ethyl stibonium inner salt

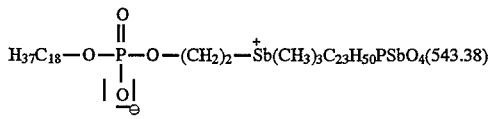

x 2 H₂O

Preparation by analogy with Example 1 from 2.1 ml (23 mmol) phosphorous oxychloride 6.49 g (24.5 mmol) octadecanol, 7+9 ml pyridine and 7.0 g (24 mmol) stibonocholine bromide. Purification by treatment with 15 g ion exchanger Amberlite® MB3 and subsequent column chromatography on silica gel with CH₂Cl₂/CH₃OH/25 percent ammonia 80:25:5. The product-containing fractions are extracted with diethylether and concentrated.
Yield: 1.0 g (8%)

| Elementary analysis: | C | H |
|---|---|---|
| calc. | 47.68% | 9.39% |
| found | 47.54% | 9.45% |
|  | 47.58% | 9.28% |

$R_F=0.62$
Thin layer chromatogram:
(chloroform/methanol/1M sodium acetate in 25 percent ammonia 70:40:10).

What is claimed is:
1. A method for the treatment of a protozoal disease caused by leishmania comprising administering to a person suffering therefrom an inhibitory amount of a compound having the following formula,

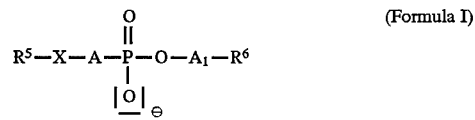

(Formula I)

wherein:

$R^5$ is a straight chain or branched alkyl group having 10–24 carbon atoms which may also contain one to three double and/or triple bonds;

A is either a single bond or is a moiety selected from the group consisting of:

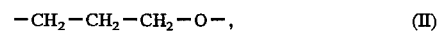 (II)

 (III)

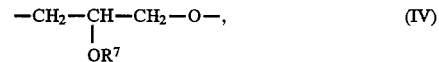 (IV)

 (V)

and

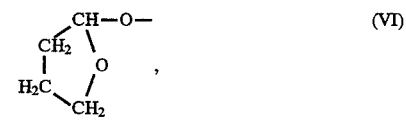 (VI)

where $R^7$ is a straight chain alkyl group having 1 to 4 carbon atoms, with the proviso that when A is a single bond, X is oxygen, sulfur or imine and that when A is any one of formula (II) to (VI), X is oxygen or sulfur, with the further proviso that when A is any one of formula (II) to (VI), A is bound to the phosphorous of formula via the oxygen atom of any one of formula (II) through (VI);

$A_1$ is a straight-chain or branched alkyl radical having 2 to 10 carbon atoms;

$R^6$ is $^{(+)}YR^8R^9R^{10}$ or has formula VII:

(Formula VII)

where Y is selected from the group consisting of p, As, Sb, and Bi and when $R^6$ is $^{(+)}YR^8R^9R^{10}$, $R^8$–$R^{10}$ may all be the same or different and are selected from the group consisting of hydrogen, straight chain alkyl groups having 1 to 6 carbon atoms and cyclic alkyl groups having 3 to 6 carbon atoms, and when $R^6$ is a substituent having formula VII, then $R^8$ and Y are defined as above, and n is 0 or 1, and W is selected from the group consisting of methylene, oxygen, imine and sulfur, with the proviso that when n=0, W is methylene when Y is P, As or Sb.

* * * * *